US00PP35065P2

(12) United States Plant Patent
Kievit et al.

(10) Patent No.: US PP35,065 P2
(45) Date of Patent: Mar. 21, 2023

(54) ***OENOTHERA* PLANT NAMED 'EVENING SUN'**

(50) Latin Name: *Oenothera missouriensis*
Varietal Denomination: Evening Sun

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/958,582

(22) Filed: Oct. 3, 2022

(51) Int. Cl.
*A01H 5/02* (2018.01)
*A01H 6/00* (2018.01)

(52) U.S. Cl.
USPC ..... Plt./460

(58) Field of Classification Search
USPC ..... Plt./263.1, 460
See application file for complete search history.

(56) References Cited

U.S. PATENT DOCUMENTS

PP29,844 P3 * 11/2018 Arnold ..... Plt./460

* cited by examiner

*Primary Examiner* — Karen M Redden
(74) *Attorney, Agent, or Firm* — Audrey Charles

(57) ABSTRACT

A new and distinct cultivar of *Oenothera* plant named 'Evening Sun', characterized by its bright yellow-colored flowers, dark grey-green colored foliage, and moderately vigorous, spreading growth habit, is disclosed.

1 Drawing Sheet

Latin name of genus and species of plant claimed: *Oenothera missouriensis.*

Variety denomination: 'Evening Sun'.

BACKGROUND OF THE INVENTION

The present invention relates to a new and distinct cultivar of *Oenothera* plant botanically known as *Oenothera missouriensis* and hereinafter referred to by the cultivar name 'Evening Sun'.

The new cultivar originated in a controlled breeding program in Hem, The Netherlands in the summer of 2016. The objective of the breeding program was the development of *Oenothera* cultivars that have attractive colored foliage, are low maintenance, and tolerate a wide range of soil types and growing conditions.

The new *Oenothera* cultivar is the result of open-pollination. The female (seed) parent of the new cultivar is the proprietary *Oenothera missouriensis* breeding selection coded A012-1, not patented, characterized by its bright yellow-colored flowers, medium grey-green colored foliage, and moderately vigorous, spreading growth habit. The male (pollen) parent of the new cultivar is unknown. The new cultivar was selected as a single flowering plant within the progeny of the above stated open-pollination during August 2017 in a controlled environment in Hem, The Netherlands.

Asexual reproduction of the new cultivar by terminal stem cuttings since August 2017 in Hem, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Evening Sun' as a new and distinct cultivar of *Oenothera* plant:

1. Bright yellow-colored flowers;
2. Dark grey-green colored foliage; and
3. Moderately vigorous, spreading growth habit.

Plants of the new cultivar differ from plants of the female parent primarily in having larger diameter flowers and narrower, more greyish-colored foliage.

Of the many commercially available *Oenothera* cultivars, the most similar in comparison to the new cultivar is 'Shimmer', U.S. Plant Pat. No. 19,663. However, in side-by-side comparisons, plants of the new cultivar differ from plants of 'Shimmer' in at least the following characteristics:

1. Plants of the new cultivar have larger diameter corollas than plants of 'Shimmer', and
2. Plants of the new cultivar have wider leaves than plants of 'Shimmer'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Evening Sun'. The plants were approximately four months old and grown three plants per pot in one-gallon containers for approximately two months in an outdoor nursery environment in West Chicago, Ill. Plants were given one pinch at approximately two weeks before transplant and another one week after transplant.

DETAILED BOTANICAL DESCRIPTION

Figure 1:
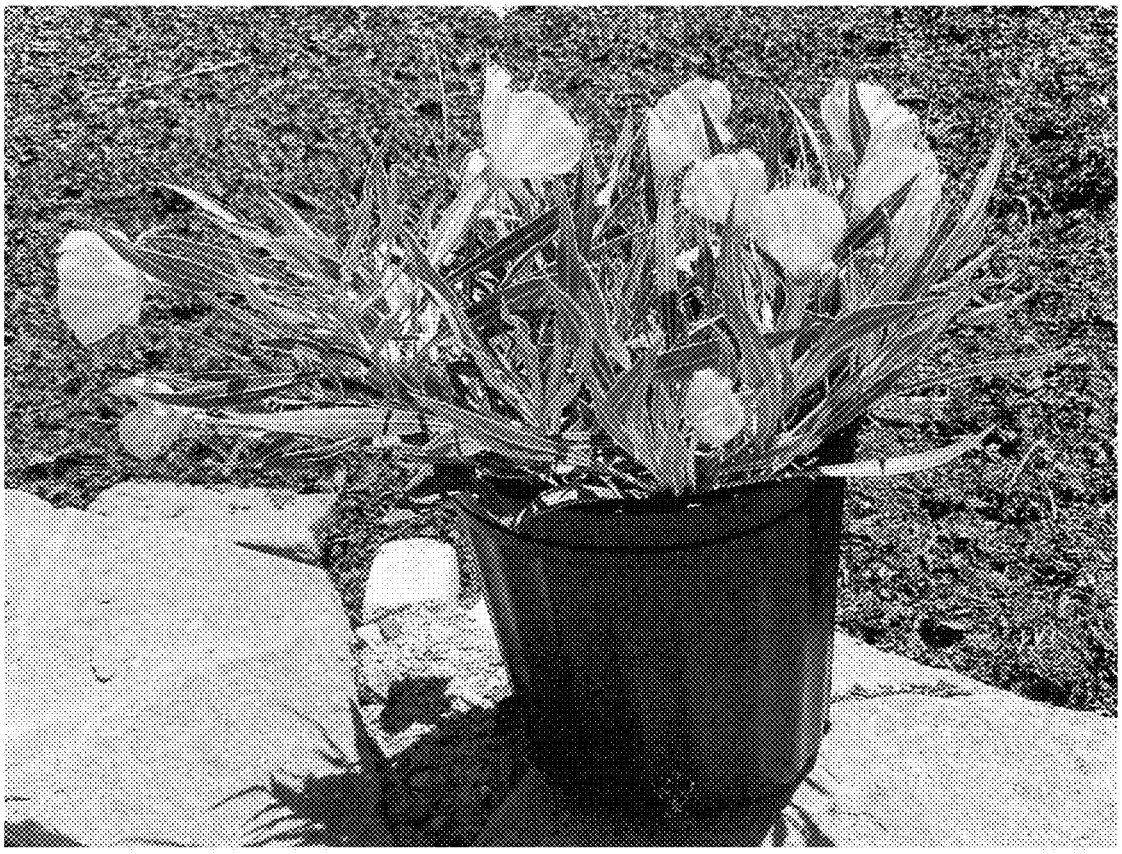
FIG. 1 illustrates a side view of the overall growth and flowering habit of 'Evening Sun'.
Figure 2:
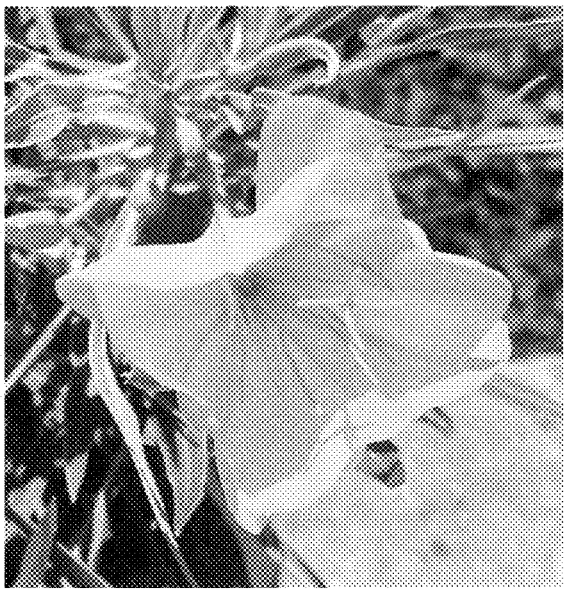
FIG. 2 illustrates a close-up view of an individual flower of 'Evening Sun'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2022 under natural light conditions in Naperville, Ill.

The following descriptions and measurements describe approximately four-month old plants produced from cuttings from stock plants and grown in a polycarbonate-covered greenhouse under conditions comparable to those used in commercial practice. Approximately six weeks after sticking, rooted plants were transplanted three plants per one-gallon containers utilizing a soilless growth medium and grown for three weeks. Plants were then transferred to an outdoor nursery environment in West Chicago, Ill. and grown for approximately two months. Plants were given one pinch at approximately two weeks before transplant and another one week after transplant. Prior to transplant plants were grown in liners in a polycarbonate greenhouse in West Chicago, Ill. Greenhouse temperatures were maintained at approximately 70° F. to 75° F. (21.1° C. to 23.9° C.) during the day and approximately 60° F. to 65° F. (15.6° C. to 18.3° C.) during the night. Supplemental lighting was used. Measurements and numerical values represent averages of typical plants.

Botanical classification: *Oenothera missouriensis* 'Evening Sun'.

Parentage:

*Female parent*.—Proprietary *Oenothera missouriensis* breeding selection coded A012-1, not patented.

*Male parent*.—Unknown.

Propagation:

*Type cutting*.—Terminal stem.

*Time to initiate roots*.—Approximately 10 to 14 days.

*Time to produce a rooted cutting*.—Approximately 42 to 45 days.

*Root description*.—Fibrous.

*Rooting habit*.—Freely branching.

Plant description:

*Commercial crop time*.—Approximately 10 to 12 weeks from a rooted cutting to finish in a 15 cm pot.

*Growth habit and general appearance*.—Herbaceous perennial; moderately vigorous, spreading growth habit.

*Hardiness*.—USDA Zone 5a (−20° F. to −15° F./−28.9 ° C. to −26° C.).

*Size*.-- Height from soil level to top of plant plane: Approximately 17.0 cm. Width: Approximately 29.0 cm.

*Branching habit*.-- Freely branching. Quantity of main branches per plant: Approximately 5.

*Branch*.—Strength: Strong, flexible. Length: Approximately 15.5 cm. Diameter: Approximately 3.0 mm. Length of central internode: Approximately 1.4 cm. Texture: Densely pubescent, tomentose. Color of young and mature stems: Appearing 193A due to NN155D pubescence covering surface of 145A, occasionally tinted with 187A.

Foliage description:

*General description*.—Fragrance: None detected. Form: Simple. Arrangement: Alternate.

*Leaves*.—Aspect: At acute angle to stem. Shape: Narrowly elliptic to narrowly obovate. Margin: Entire to widely and shallowly dentate, occasionally wavy. Apex: Acute. Base: Attenuate. Venation pattern: Pinnate. Length of mature leaf: Approximately 8.5 cm. Width of mature leaf: Approximately 1.0 cm to 1.5 cm. Texture of upper and lower surfaces: Densely pubescent, tomentose. Color of upper and lower surfaces of young foliage: 189A with an overlay of NN155D and midvein of NN155C. Color of upper surface of mature foliage: 189A with midvein of NN155C. Color of lower surface of mature foliage: 189A with an overlay of NN155D and midvein of NN155C.

*Petiole*.—Length: Approximately 1.5 cm. Diameter: Approximately 2.0 mm to 3.0 mm. Texture: Densely pubescent, tomentose. Color: Appearing 193A due to NN155D pubescence covering surface of 145A.

Flowering description:

*Flowering habit*.—'Evening Sun' is day length neutral flowering under outdoor growing conditions with substantially continuous blooming from spring through summer.

*Lastingness of individual flower on the plant*.—Approximately 5 to 7 days.

Flower description:

*General description*.—Type: Single. Quantity per plant: Approximately 3. Aspect: Facing outward to upward. Fragrance: None detected.

*Bud*.—Quantity per plant: Approximately 4.

*Bud just before opening*.—Shape: Lanceolate with a tubular hypanthium. Length including hypanthium: Approximately 11.0 cm (hypanthium approximately 7.0 cm). Diameter: Approximately 8.0 mm. Texture: Densely pubescent, tomentose. Color: Appearing 193A due to NN155D pubescence covering surface of 145A.

*Corolla*.—Shape: Cupped above a tubular hypanthium, overlapping in a single whorl. Diameter: Approximately 5.5 cm. Depth: Approximately 3.5 cm.

*Petals*.—Quantity: 4. Shape: Obovate. Margin: Entire. Apex: Obtuse to slightly emarginate, slightly ruffled. Base: Truncate. Length: Approximately 3.5 cm. Width: Approximately 4.2 cm. Texture of upper and lower surfaces: Glabrous. Color of upper surface when first and fully open: 2A. Color of lower surface when first and fully open: 2B.

*Calyx*.—Shape: Subtending, reflexed with upper half fused except for tips. Diameter at distal end: Approximately 1.0 cm. Depth: Approximately 3.0 cm.

*Sepals*.—Quantity per flower: 4. Shape: Lanceolate. Apex: Acuminate. Base: Truncate. Length: Approximately 3.5 cm. Width: Approximately 4.0 mm. Texture of upper (inner) surface: Sparsely pubescent. Texture of lower (outer) surfaces: Densely pubescent, tomentose. Color of upper (inner) surface: 146D with 145B. Color of lower (outer) surface: Appearing 193A due to NN155D pubescence covering surface of 145A.

*Peduncle*.—Strength: Strong, flexible. Aspect: Acute angle to stem. Length: Approximately 0.5 mm to 1.0 cm. Diameter: Approximately 2.0 mm. Texture:

Densely pubescent, tomentose. Color: Appearing 193A due to NN155D pubescence covering surface of 145A.

*Reproductive organs*.—Androecium: Stamen quantity: 8, inserted at the top of the hypanthium, anther attached to filament at midpoint resulting in a T-shaped appearance. Stamen length: Approximately 2.3 cm. Filament length: Approximately 2.2 cm. Filament color: 154C. Anther shape: Slender elongate. Anther length: Approximately 1.2 cm. Anther color: 12C. Pollen amount: Sparse. Pollen color: 155D. Gynoecium: Pistil quantity: 1 per flower. Pistil length: Approximately 14.0 cm (hypanthium of approximately 11.5 cm). Hypanthium width: Approximately 2.0 mm with 1.0 cm at distal end. Stigma shape: 4 lobed, rotate. Stigma lobe length: Approximate 5.0 mm. Stigma color: 154B. Style length: Approximately 12.0 cm. Style color: 154C. Ovary length: Approximately 2.0 cm. Ovary color: Appearing 191D due to NN155D pubescence covering surface of 146D.

Seed and fruit production: Neither seed nor fruit production has been observed.

Disease and pest resistance: Resistance to pathogens and pests common to *Oenothera* has not been observed.

What is claimed is:

1. A new and distinct cultivar of *Oenothera* plant named 'Evening Sun', substantially as herein illustrated and described.

* * * * *